United States Patent [19]

Cleveland et al.

[11] Patent Number: 4,974,010
[45] Date of Patent: Nov. 27, 1990

[54] FOCUS CONTROL SYSTEM

[75] Inventors: Dixon Cleveland, Vienna; James H. Cleveland, Clifton; Peter L. Norloff, Fairfax, all of Va.; Jeffrey A. Forsythe, West Chester, Pa.

[73] Assignee: LC Technologies, Inc., Fairfax, Va.

[21] Appl. No.: 363,716

[22] Filed: Jun. 9, 1989

[51] Int. Cl.⁵ .......................... G03B 3/10; G03B 29/00
[52] U.S. Cl. ...................... 354/403; 354/62; 354/210; 351/210
[58] Field of Search .................. 354/400, 402, 403, 62; 351/210, 209

[56] References Cited

U.S. PATENT DOCUMENTS

| | | | |
|---|---|---|---|
| 3,617,128 | 11/1971 | Harvey | 356/4 |
| 3,804,496 | 4/1974 | Crane et al. | 351/6 |
| 3,864,030 | 2/1975 | Cornsweet | 351/7 |
| 3,869,694 | 3/1975 | Merchant | 340/16 R |
| 4,003,642 | 1/1977 | Vogeley | 351/6 |
| 4,199,785 | 4/1980 | McCullough et al. | 358/180 |
| 4,231,066 | 10/1980 | Merchant | 358/180 |
| 4,251,139 | 2/1981 | Matsumura | 351/7 |
| 4,287,410 | 9/1981 | Crane et al. | 250/201 |
| 4,373,787 | 2/1983 | Crane et al. | 351/210 |
| 4,544,246 | 10/1985 | Crane et al. | 351/211 |
| 4,626,089 | 12/1986 | Takahashi et al. | 351/208 |
| 4,635,203 | 1/1987 | Merchant | 364/458 |
| 4,648,052 | 3/1987 | Friedman et al. | 364/550 |
| 4,673,264 | 6/1987 | Takahashi | 351/211 |
| 4,678,297 | 7/1987 | Ishikawa et al. | 351/208 |
| 4,695,959 | 9/1987 | Lees et al. | 364/458 |
| 4,725,722 | 2/1988 | Maeda et al. | 250/201 |
| 4,755,045 | 7/1988 | Borah et al. | 351/210 |
| 4,756,613 | 7/1988 | Okashita | 351/206 |
| 4,789,235 | 12/1988 | Borah et al. | 351/246 |

OTHER PUBLICATIONS

A. Downing, "Eye Controlled and Other Fast Communicators for Speech Impaired and Physically Handicapped Persons", *Australasian Phys. & Engg. Scis in Med.* vol. 8, No. 1, pp. 17-21 (1985).

J. Levine et al., "Performance of an Eyetracker for Office Use", *Comput. Biol. Med.* vol. 14, No. 1, pp. 77-89 (1984).

J. Merchant et al., "A Remote Oculometer Permitting Head Movement", Report No. AMRL-TR-73-69, Aerospace Medical Research Laboratory, Air Force Systems Command, Dayton, Ohio (Oct. 1973).

L. Young et al., "Survey of Eye Movement Recording Methods", Behavior Research *Methods and Instrumentation,* vol. 7, No. 5, pp. 397-429 (1975).

M. Friedman et al., "The Eyetracker Communication System", John Hopkins APL Technical Digest vol. 3, No. 3, pp. 250-252 (1982).

R. Razdan et al., "Eye Tracking for Man/Machine Interfaces", Sensors, pp. 39-42ff (Sep. 1988).

Anon., "ISCAN® Eye Movement Monitoring and Pupillometry Systems 1988-89 Catalogue", ISCAN Inc. (1986).

Anon., "Eye-Trac®: Field Proven Systems for Quantitative Analysis of Eye Movement, Pupillometry, and Visual Function", Applied Science Laboratories (1982).

*Primary Examiner*—Michael L. Gellner
*Attorney, Agent, or Firm*—Kirkland & Ellis

[57] ABSTRACT

A system for focussing a lens on a point light source is provided that includes an opaque member disposed near the lens. The member cast a shadow having a distinguishable orientation in the image of the light source. An image processing device determines the focus condition and range to the point light source from the orientation and size of the shadow.

8 Claims, 4 Drawing Sheets

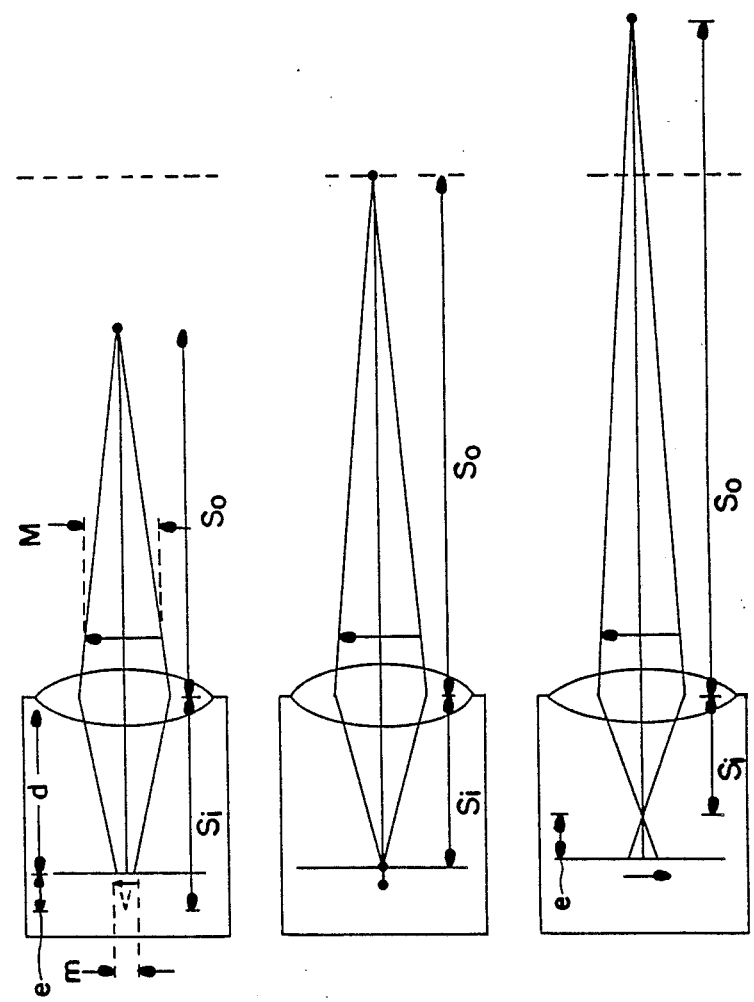

FOCUS CONTROL SYSTEM

BACKGROUND

The present invention relates to systems for determining the focus condition of a lens, controlling the focus of the lens, and finding a range to an object.

In many imaging applications, it is often desired to focus a lens or other collector on an object and to maintain the lens sharply focussed despite the object's longitudinal motion, i.e., motion along the optical axis of the lens. One such imaging application is eye-gaze tracking in which an apparatus determines the point in space at which the eye is looking.

Prior eye-gaze trackers are disclosed in U.S. Pat. Nos. 3,864,030 to Cornsweet; 4,287,410 and 4,373,787 to Crane et al.; 4,648,052 to Friedman et al.; and in certain U.S. patent applications of Thomas E. Hutchinson, Ser. Nos. 07/086,809; 07/267,266, filed Nov. 4, 1988; and 07/326,787. Those systems typically illuminate the eye with infrared light which is reflected from various parts of the eye, particularly the cornea and retina, to an imaging device such as a videocamera. The spatial relations between the reflections are used to determine the gaze point. For example, the corneal reflection moves about eighty micrometers per degree of eye rotation with respect to the pupil reflection.

From elementary geometry, it will be appreciated that the location finding accuracy of such trackers is heavily dependent on accurately locating the eye reflections with respect to the apparatus and with respect to each other. Thus, the gaze point accuracy can be improved by maintaining the camera sharply focussed on the eye.

One (uncomfortable) way of keeping the camera focussed is by preventing relative motion of the eye and camera, e.g., by restraining the eye or head of the user. Another way is by providing an autofocus mechanism to the camera. (If lateral motions of the eye, i.e., motions perpendicular to the optical axis, exceed the camera's instantaneous field of view, a lateral tracking mechanism is also needed.) The above-cited U.S. patents describe two types of autofocus mechanism whereby longitudinal eye displacements are detected using the corneal reflection of a light source. In the patent to Cornsweet, a variable amplitude modulation due to motion of the source's image formed between two chopper wheels is detected. In the patents to Crane et al., the difference in output between two detectors longitudinally equidistant, when properly focussed, from the source's image is detected. U.S. Pat. No. 3,869,694 to Merchant et al. describes an improved eyegaze tracker that includes an ultrasonic position measuring system that is used to adjust the focus of the tracker.

Other devices for focussing an imaging device on an eye are disclosed in U.S. Pat. Nos. 4,251,139 to Matsumura; 4,626,089 to Takahashi et al.; 4,673,264 to Takahashi; and 4,678,297 to Ishikawa et al. The patents to Ishikawa et al. and Matsumura disclose optical system focussing and alignment by projecting a mark image onto the cornea and detecting the reflected mark image. The patents to Takahashi et al. and Takahashi disclose projecting a mark image into the eye and detecting the mark image reflected from the retina.

Those devices and other mechanisms such as multi-camera-parallax devices are unsuitable for many gaze trackers and other applications because they typically require additional equipment and complex calibration, and may not provide the required range measurement accuracy. In addition, they can excessively restrict the freedom of motion of the user.

Accordingly, it is an object of the present invention to provide an apparatus for determining the focus condition of a lens. It is another object of the invention to provide a head tracker which accurately maintains a clear image of a user's eye for determining the user's gaze point. It is a further object of the present invention to provide a head tracker which accurately determines the range to the user's eye.

SUMMARY

In accordance with the present invention, there is provided a focus analysis system comprising a camera including a lens and a means for sensing an image formed by the lens, a point light source, an image of the point light source being formed by the lens, an opaque member disposed near the lens, the opaque member giving the image of the point light source a distinguishable orientation, and an image processor in communication with the sensing means, the image processor analyzing the focus condition of the lens based on the distinguishable orientation of the image.

BRIEF DESCRIPTION OF THE DRAWINGS

The various objects and advantages of the present invention will become more apparent after a reading of the following detailed description in conjunction with the drawings in which:

FIGS. 3a, 3b, and 3c are ray diagrams illustrating part of the apparatus of FIG. 1;

DETAILED DESCRIPTION

The following description is framed in terms of a system employing a camera to track a user's eye while the user's head is in motion. As the head moves toward and away from the camera, i.e., longitudinally along the optical axis of the camera, the corneally reflected image of a point light source is kept sharply focussed by the camera, thereby tracking head motions. Those of ordinary skill in the art will understand that, although light cameras and refractive optics are described, the present invention comprehends all imaging systems, such as those employed in tomography, seismology, radar, etc. Thus, "light" will be understood to refer to all wave phenomena, such as electromagnetic and acoustic energies, and "camera" will be understood to refer to any device which forms images from waves it collects.

Figure 1:
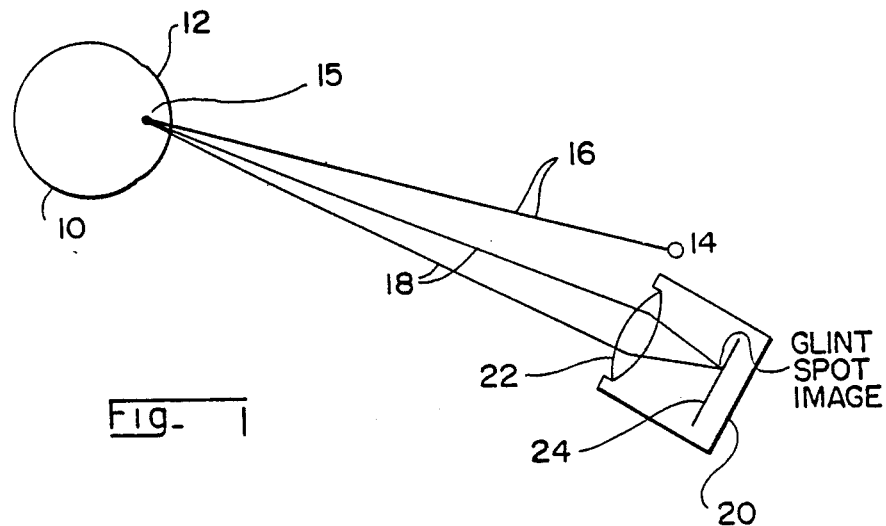
FIG. 1 shows an arrangement of an apparatus in accordance with the invention with respect to a user's eye.

In an eye-tracking system, keeping the camera focussed on the eye is equivalent to determining the len's focus condition, i.e., the magnitude and direction of the longitudinal adjustment of the lens needed to focus an image at a fixed position in the camera. Typically, an image sensor such as a photographic film, focal plane detector array, or vidicon tube is located at the fixed position. Referring to the figures in all of which like parts have like reference numerals, FIG. 1 illustrates the geometry of an apparatus in accordance with the present invention.

Eye 10 having cornea 12 is illuminated by a point light source 14 disposed at a suitable distance. Light rays 16 strike cornea 12, and rays 18 are reflected toward camera 20 having a lens or other collector 22. The collector 22 forms an image on a suitable sensor 24 disposed in its focal plane. A tiltable mirror (not shown) may also be provided to reflect the field of view of camera 20 toward eye 16. The mirror may be controlled as described in co-pending U.S. patent application Ser. No. 07/363,862, filed Jun. 9, 1989 for Method and Apparatus for Mirror Control, incorporated herein by reference to track lateral movement of source 14.

It is well known that in the visible and near-infrared portion of the electromagnetic spectrum about 2.5% of the incident light is reflected by the outer corneal surface due to the difference between the refractive indices of air and the cornea. Accordingly, the cornea acts like a convex mirror having a radius of curvature of about 7 mm, and reflected rays 18 form a glint spot on the eye that appears to emanate from an image 15 of source 14 located a few millimeters behind the outer corneal surface. Image 15 is virtual, i.e., no luminous image of source 14 would appear on a screen at its apparent location, and is known as the first Purkinje image. It will be appreciated that a real point source, a real image of a point source, and a virtual image of a point source are suitable for use in the present invention.

If the lens 22 is sharply focussed on eye 10, the reflected rays 18 will be brought to nearly a point or small area on sensor 24. As the lens goes out of focus, the area of the reflected rays 18 on sensor 24 increases, viz., the image of the glint spot blurs. Since the glint image blurs equally as the lens focusses behind and before the eye 10, measuring the size of the glint spot, although it is proportional to the focus condition of the camera lens, is insufficient to determine the focus condition unambiguously.

Figure 2:
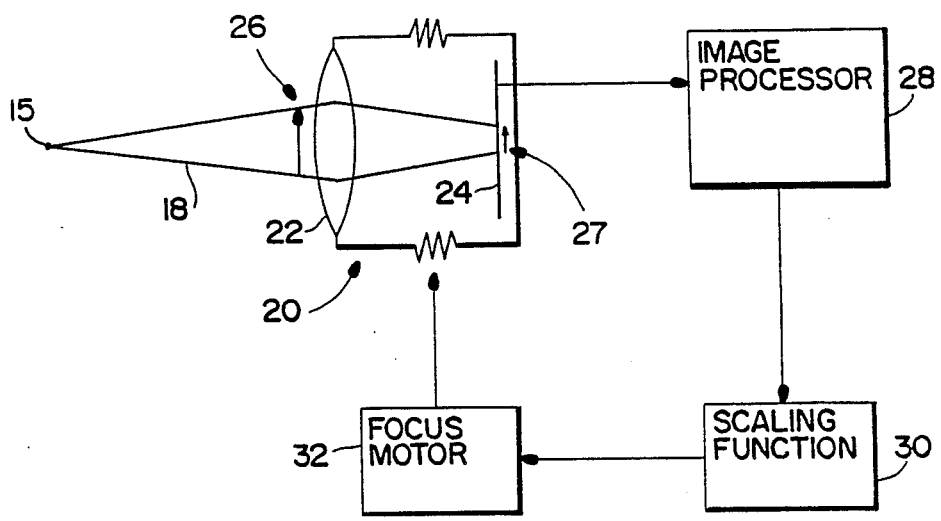
FIG. 2 shows details of the apparatus in accordance with the present invention.

In accordance with the present invention, an opaque member 26 is disposed near, e.g., on, the surface of lens 22 that casts a shadow having a distinguishable orientation in the glint spot image formed on sensor 24. It will also be appreciated that opaque member 26 can be disposed in lens 22, e.g., by positioning it between elements of a multi-element lens; therefore, "near" will be understood to comprehend all such positions. Referring to FIG. 2, a suitable opaque member 26 is an arrow-like form that casts shadow 27 on sensor 24. (Shadow 27 is shown behind sensor 24 in FIG. 2 for clarity.) As described in more detail below, the orientation and size of shadow 27 unambiguously determine the focus condition of lens 22. It will be appreciated that many other forms are suitable for opaque member 26, including irregularly shaped lens apertures, most letters of the alphabet, arabic numerals, etc. In addition, it will be appreciated that the present invention also comprehends the examination of a bright image region having suitably determinable size and orientation. Suitable forms are those which are distinguishable when inverted through any lateral direction.

As shown in FIG. 3a, when camera 20 is focussed behind eye 10 (or eye 10 has moved closer to camera 20), the sharpest image of the glint spot falls behind the sensor 24; thus, the glint spot's blurred image on sensor 24 includes an erect shadow 27 of opaque member 26. When camera 20 is sharply focussed on eye 10 as shown in FIG. 3b, the shadow 27 collapses in the image of the glint spot that is of somewhat diminished intensity as a result. When camera 20 is focussed before eye 10 as shown in FIG. 3c, the glint spot's blurred image on sensor 24 includes an inverted shadow 27 of opaque member 26.

It will be appreciated that the sizes of both the glint spot and shadow 27 on sensor 24 are proportional to the amount of defocus of lens 22. In addition, the resolution of camera 20, the angular subtent of the point source such as virtual image 15, and the relative positions of opaque member 26 and lens 22 affect the determination of the focus condition. For example, a light source is sufficiently point-like and an opaque member is suitably positioned when the member's shadow is sharp enough to be resolved by the camera.

Once the lens is focussed, the distance between the camera and the point source or virtual image 15 is determinable from the Gaussian lens formula:

$$1/s_o + 1/s_i = 1/f$$

where $s_o$ is the distance from lens 22 to image 15 and eye 10; $s_i$ is the distance from lens 22 to the image of image 15; and f is the effective focal length of the lens. It will be understood that greater accuracy may be achieved if needed by replacing the Gaussian lens formula with an appropriate thick-lens or other equation. Since $s_i$ can be determined from the construction of camera 20 in ways that are well known, the unknown distance $s_o$, i.e., the range from the camera to the eye, is determined. Furthermore, it will be understood that the depth of field of the lens affects the precision with which the range can be computed. A narrow depth of field can permit more precise range measurements because a given amount of blurring of the image occurs for lesser longitudinal eye motion.

Referring again to FIG. 2, an image processor 28 receives output signals from sensor 24 and analyzes the focus condition of lens 22 based on the size and orientation of shadow 27. A suitable camera is the Model VDC-3860 made by Sanyo and a suitable lens is the Model V7514 75-mm f/1.4 lens made by Computar. A suitable image processor 28 comprises a frame grabber, such as the PC VISION frame grabber board made by Imaging Technology, Inc., Woburn, MA, or other image acquisition board, a computer, such as the DESKPRO-286 computer made by Compaq with a 287 math co-processor, and an image analysis program. It will be appreciated that the interface of the computer and frame grabber and the characteristics of the image analysis program, beyond their ability to determine the size and orientation of shadow 27, are not critical to the present invention. The size and orientation of shadow 27 are applied in a suitable controller 30 to operate a conventional motor or other drive mechanism 32 to vary the focus of lens 22.

Figure 4A:
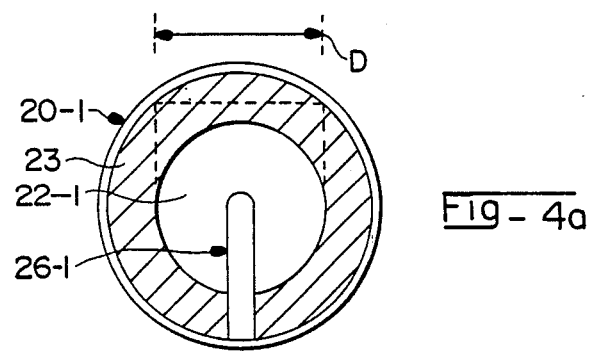
FIG. 4a, shows one embodiment of an opaque member.
Figure 4B:
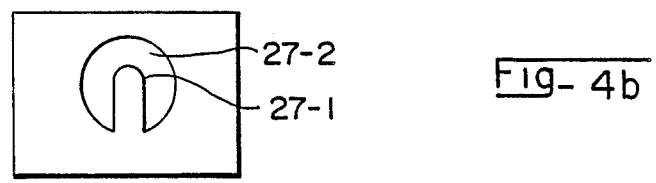
FIGS. 4b and 4c show inverted and uninverted shadows of the member when the lens is focussed behind and before a point light source.
Figure 4C:
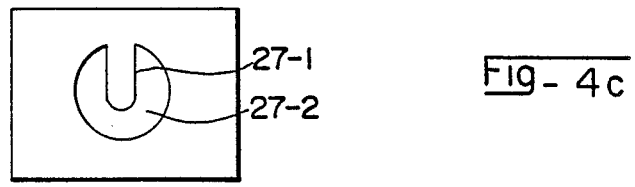

The image analysis program which determines the lens's focus condition must accommodate the specific shape of the opaque member 26 which casts shadow 27 within the image of the point light source. Another embodiment of a suitable opaque member, shown in FIG. 4a, is a strip 26-1 extending from lens housing 20-1 over the lens 22 to about the center of the lens aperture 22-1 formed by iris 23. In FIG. 4a, strip 26-1 is shown extending vertically from the bottom, but it will be understood that any orientation is acceptable so long as it is known to the focus analysis program. FIGS. 4b and 4c show the uninverted and inverted shadows 27-1 of strip 26-1 when lens 22 is focussed behind and before the light source, respectively. It will be understood that the size and orientation of shadow 27-1 or of bright portion 27-2 can be used to determine the focus condition of lens 22.

It will be appreciated that many image processing programs are available that implement feature extraction and location techniques which can be used with the present invention. A suitable image processing method to determine the orientation of the shadow comprises three steps. First, a 2-dimensional region around the point source image is selected, and the centroid of the image's intensity profile is computed in a conventional way. It will be understood that by centroid is meant the simple average of the pixel locations that can be selected by comparing their intensity values to a predetermined threshold. Other methods for locating image features that use weighted averages of pixels exceeding predetermined thresholds are described in co-pending U.S. patent application Ser. No. 07/863,873, filed Jun. 9, 1989 for Method and Apparatus for Locating Image Features which is incorporated here by reference. The locations of the 2-dimensional centroids are indicated by the x's in FIGS. 5a and 5b.

Figure 5A:
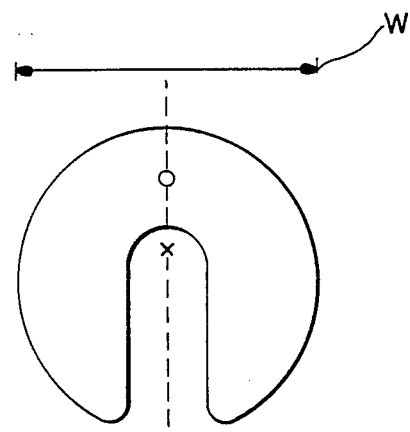
FIGS. 5a and 5b illustrate the operation of an image processing procedure used to analyze whether the shadow is uninverted or inverted.
Figure 5B:
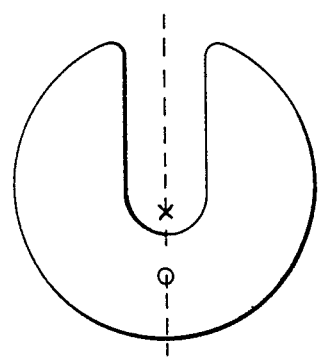

Second, a 1-dimensional cut through the 2-dimensional centroid point along a line parallel to strip 26-1 is taken, and the centroid of the pixel intensity profile is taken along that cut to determine which side of the light source image is blocked by strip 26-1. The dashed lines in FIGS. 5a and 5b show the paths of the 1-dimensional cuts through the 2-dimensional centroids, and the o's indicate the intensity centroids taken along those cuts.

Third, the relative positions of the 1-dimensional and 2-dimensional centroids are determined. As shown in FIG. 5a, if the 1-dimensional centroid is above the 2-dimensional centroid (for a vertically oriented opaque member), shadow 27-1 is determined to be uninverted, and the lens is known to be focussed behind the source. Conversely, if the 1-dimensional centroid is below the 2-dimensional centroid, as shown in FIG. 5b, shadow 27-1 is determined to be inverted, and the lens is known to be focussed before the source.

It will be appreciated that to control a lens to bring an object into focus, it is necessary to know how to change the lens setting, i.e., whether to increase or decrease a distance d between the lens plane and the image sensor plane (see FIGS. 3a-c). As can be seen from the Gaussian lens equation and as illustrated in the figures, the lens setting d should be increased if the lens is determined to be focussed behind the light source and decreased if it is focussed before the light source.

With the direction of the focus correction known, the magnitude of the lens adjustment needed can be determined as follows. Referring again to FIGS. 3a-c, it can be seen by reason of similar triangles that magnitude m of the shadow 27 cast upon the camera sensor plane is proportional to axial error e in the lens setting. Calling M the magnitude of opaque member 26 and recalling that the ideal lens setting is $s_i$, the equation relating the shadow magnitude m, which can be determined in a conventional way, to the axial error e is:

$$M/s_i = m/e$$

It will be understood that the foregoing equation is approximate if the opaque member 26 is not in the lens plane and can be mathematically corrected if desired. Since $s_i$ is just the sum of the current lens setting d and the axial error e, the required lens correction, i.e., the axial error e, in terms of the measured shadow magnitude m, the known present lens setting d, and the known opaque member size M is given by:

$$e = md/(M-m)$$

With reference to FIG. 2, the lens error e is used in the scaling function 30 for computing an error command for focus motor 32 in an automatic focus control system.

For purposes of measuring only the magnitude, not the direction, of the lens setting error e, it is not necessary to use an opaque member or irregular aperture of distinguishable orientation. The round aperture of a typical lens fully suffices as long as the lens's aperture diameter D generally set by iris 23 is known to the focus analysis program. In this case, the aperture diameter D replaces the opaque member size M, and a suitable procedure for measuring the shadow size m consists of measuring the diameter of the image of the light source on the camera sensor plane. When using the aperture/opaque-member configuration of FIG. 4a where the vertical characteristics of the image are used to determine the polarity or direction of the focus condition, the horizontal characteristics of the shadow may be used for magnitude measurement purposes. As illustrated in FIGS. 5a and 5b, the width w of the aperture image may be measured by taking a horizontal cut through the 2-dimensional centroid, detecting the outside edges of the aperture image, and calculating the aperture image width from the difference between the right and left edge coordinates.

Although the width of the aperture image theoretically collapses to zero when the point light source is in sharp focus, the finite size of any real light source and the limited resolution of the image sensor cause the aperture image to reduce to a minimum size when the lens is in focus. In practice, the image width measured as described above should be adjusted by subtracting the minimum image size from it. In the last equation above, the adjusted aperture image width is substituted for m and the aperture diameter D is substituted for M.

The description of the present invention is intended in all senses to be illustrative rather than restrictive. Those of ordinary skill in the art will recognize various modifications and embodiments that are intended to be included in the spirit and scope of the invention that is to be limited solely by the following claims.

What is claimed is:

1. A focus analysis system comprising:
   a camera including a lens and means for sensing an image formed by the lens;
   a point light source, an image of the point light source being formed by the lens;
   an opaque member disposed near the lens, the opaque member giving the image of the point light source a distinguishable orientation; and
   an image processor in communication with the sensing means, the image processor analyzing the focus condition of the lens based on the distinguishable orientation of the image.

2. The system of claim 1, wherein the image processor analyzes the focus condition based on the distinguishable orientation of a shadow of the opaque member in the image.

3. A range finding system comprising:
a camera including a variable focus lens and means for sensing an image formed by the lens;
a point light source, an image of the point light source being formed by the lens;
an opaque member disposed near the lens, the opaque member giving a distinguishable orientation to the image of the point light source; and
an image processor in communication with the sensing means, the image processor finding a range from the camera to the point light source based on the magnitude and orientation of the image of the point light source.

4. The system of claim 3, wherein the image processor finds the range based on the magnitude and orientation of a shadow of the opaque member in the image of the point light source.

5. A focus control system comprising:
a camera including a variable focus lens, means for varying the lens focus, and means for sensing an image formed by the lens;
a point light source, an image of the point light source being formed by the lens;
an opaque member disposed near the lens, the opaque member giving a distinguishable orientation to the image of the point light source; and
an image processor in communication with the sensing means and the varying means, the image processor analyzing the focus condition of the lens based on the distinguishable orientation and size of the image and causing the varying means to maintain the lens in a focussed condition.

6. The system of claim 5, wherein the image processor analyzes the focus condition of the lens based on the distinguishable orientation and size of a shadow of the opaque member in the image.

7. A method of focus analysis comprising the steps of:
forming an image of a point light source with a lens;
disposing an opaque member near the lens; and
determining the focus condition of the lens from a distinguishable orientation of the image produced by the opaque member.

8. The method of claim 7, wherein the focus condition is determined from a distinguishable orientation of a shadow of the opaque member in the image.

* * * * *